US006977164B2

(12) United States Patent
WalkerPeach et al.

(10) Patent No.: US 6,977,164 B2
(45) Date of Patent: Dec. 20, 2005

(54) COMPOSITIONS AND KITS FOR HERPES SIMPLEX VIRUS TYPE 1 AND 2 NUCLEIC ACID DETECTION

(75) Inventors: Cindy WalkerPeach, Austin, TX (US); Dwight DuBois, Austin, TX (US)

(73) Assignee: Stratagene California, La Jolla, CA (US)

( * ) Notice: Subject to any disclaimer, the term of this patent is extended or adjusted under 35 U.S.C. 154(b) by 61 days.

(21) Appl. No.: 10/984,301

(22) Filed: Nov. 9, 2004

(65) Prior Publication Data

US 2005/0112561 A1    May 26, 2005

Related U.S. Application Data

(62) Division of application No. 09/594,065, filed on Jun. 14, 2000.

(51) Int. Cl.$^7$ .............................................. C12P 19/34
(52) U.S. Cl. ................. 435/91.33; 435/91.1; 435/91.2; 536/23.72; 536/25.32; 514/44
(58) Field of Search ............................. 435/91.1, 91.2, 435/91.33; 536/23.72, 25.32; 514/44

(56) References Cited

OTHER PUBLICATIONS

McNab et al., Journal of Virology, vol. 72, No. 2, Feb. 1998, p. 1060-1070.*

* cited by examiner

*Primary Examiner*—Laurie Scheiner
(74) *Attorney, Agent, or Firm*—Kathleen M. Williams; Palmer & Dodge LLP

(57) ABSTRACT

The invention relates to polynucleotides for HSV detection and the use of these polypeptides in kits and methods for HSV detection.

14 Claims, 9 Drawing Sheets

FIGURE 1

HSV-1

5'-*tcaccaccgtcagcaccttc*atcgacctgaacatcaccat<u>gctggagga</u>T<u>cacgagtttgt</u>cccctggaggtgtacacgc
gccacgagat*caaggacagcggcctgct*-3'

HSV-2

5'-*tcaccaccgtcagcaccttc*atcgacctgaacatcaccat<u>gctggagga</u>C<u>cacgagtttgt</u>gccctggaggtgtacacgc
gccacgagat*caaggacagcggcctgct*-3'

IAC

5'-*tcaccaccgtcagcaccttc*tagagcaccgcccacatgtggaggtcccctgtttgagcact<u>aggaggtcgtaccactaca</u>
actccagcta*caaggacagcggcctgct*-3'

SEQUENCE LISTING

<160> NUMBER OF SEQ ID NOS: 14

<210> SEQ ID NO 1
<211> LENGTH: 20
<212> TYPE: DNA
<213> ORGANISM: Artificial
<220> FEATURE:
<223> OTHER INFORMATION: Forward PCR primer

<400> SEQUENCE: 1
tcaccaccgt cagcaccttc                    20

<210> SEQ ID NO 2
<211> LENGTH: 18
<212> TYPE: DNA
<213> ORGANISM: Artificial
<220> FEATURE:
<223> OTHER INFORMATION: Reverse PCR primer

<400> SEQUENCE: 2
agcaggccgc tgtccttg                      18

```
<210> SEQ ID NO 3
<211> LENGTH: 30
<212> TYPE: DNA
<213> ORGANISM: Artificial
<220> FEATURE:
<223> OTHER INFORMATION: IAC specific molecular beacon

<400> SEQUENCE: 3
ccctgcgtag tggtacgacc tcctgcaggg                              30

<210> SEQ ID NO 4
<211> LENGTH: 33
<212> TYPE: DNA
<213> ORGANISM: Artificial
<220> FEATURE:
<223> OTHER INFORMATION: HSV-type common (TC) moleculear beacon

<400> SEQUENCE: 4
ccctgcaaac tcgtgktcct ccagcatgca ggg                          33

<210> SEQ ID NO 5
<211> LENGTH: 29
<212> TYPE: DNA
<213> ORGANISM: Artificial
<220> FEATURE:
<223> OTHER INFORMATION: Single stranded oligonucleotide target for
      IAC-specific molecular beaco

<400> SEQUENCE: 5
agcactagga ggtcgtacca ctacaactc                               29

<210> SEQ ID NO 6
<211> LENGTH: 39
<212> TYPE: DNA
<213> ORGANISM: Artificial
<220> FEATURE:
<223> OTHER INFORMATION: Single stranded oligonucleoitde molecular
      beacon target for HSV type-

<400> SEQUENCE: 6
aacatcacca tgctggagga tcacgagttt gtccccctg                    39

<210> SEQ ID NO 7
<211> LENGTH: 39
<212> TYPE: DNA
<213> ORGANISM: Artificial
<220> FEATURE:
<223> OTHER INFORMATION: Single stranded oligonucleotide molecular
      beacon target for HSV type-

<400> SEQUENCE: 7
aacatcacca tgctggagga ccacgagttt gtccccctg                    39

<210> SEQ ID NO 8
<211> LENGTH: 74
<212> TYPE: DNA
<213> ORGANISM: Artificial
<220> FEATURE:
<223> OTHER INFORMATION: Forward primer for synthesis of IAC

<400> SEQUENCE: 8
atcgaattct caccaccgtc agcaccttct agagcaccgc ccacatgtgg aggtcccct   60 gtttgagcac tagg                                               74
```

<210> SEQ ID NO 9
<211> LENGTH: 73
<212> TYPE: DNA
<213> ORGANISM: Artificial
<220> FEATURE:
<223> OTHER INFORMATION: Reverse primer for synthesis of IAC

<400> SEQUENCE: 9
atcgaattca gcaggccgct gtccttgtag ctggagttgt agtggtacga cctcctagtg    60
ctcaaacagg ggg    73

<210> SEQ ID NO 10
<211> LENGTH: 33
<212> TYPE: DNA
<213> ORGANISM: Artificial
<220> FEATURE:
<223> OTHER INFORMATION: HSV type-1 specific molecular beacon

<400> SEQUENCE: 10
ccctgcaaac tcgtgttcct ccagcatgca ggg    33

<210> SEQ ID NO 11
<211> LENGTH: 33
<212> TYPE: DNA
<213> ORGANISM: Artificial
<220> FEATURE:
<223> OTHER INFORMATION: HSV type-2 specific molecular beacon

<400> SEQUENCE: 11
ccctgcaaac tcgtgctcct ccagcatgca ggg    33

<210> SEQ ID NO 12
<211> LENGTH: 109
<212> TYPE: DNA
<213> ORGANISM: Artificial
<220> FEATURE:
<223> OTHER INFORMATION: Sequence amplified by PCR reaction for HSV
      type-1

<400> SEQUENCE: 12
tcaccaccgt cagcaccttc atcgacctca acatcaccat gctggaggat cacgagtttg    60
tccccctgga ggtgtacacc cgccacgaga tcaaggacag cggcctgct    109

<210> SEQ ID NO 13
<211> LENGTH: 109
<212> TYPE: DNA
<213> ORGANISM: Artificial
<220> FEATURE:
<223> OTHER INFORMATION: Sequence amplified by PCR for HSV type-2

<400> SEQUENCE: 13
tcaccaccgt cagcaccttc atcgacctga acatcaccat gctggaggac cacgagtttg    60
tgcccctgga ggtctacacg cgccacgaga tcaaggacag cggcctgct    109

<210> SEQ ID NO 14
<211> LENGTH: 109
<212> TYPE: DNA
<213> ORGANISM: Artificial
<220> FEATURE:
<223> OTHER INFORMATION: Sequence amplified by PCR for IAC -continued

```
<400> SEQUENCE: 14
tcaccaccgt cagcaccttc tagagcaccg cccacatgtg gaggtccccc tgtttgagca        60
ctaggaggtc gtaccactac aactccagct acaaggacag cggcctgct                   109
```

US 6,977,164 B2

COMPOSITIONS AND KITS FOR HERPES SIMPLEX VIRUS TYPE 1 AND 2 NUCLEIC ACID DETECTION

RELATED APPLICATIONS

This application is a divisional of U.S. application Ser. No. 09/594,065, filed Jun. 14, 2000.

FIELD OF THE INVENTION

The present invention relates to novel polynucleotides, molecular beacons, methods and kits for the detection of herpes simplex virus types 1 and 2.

BACKGROUND OF THE INVENTION

Herpes Simplex Virus (HSV) type-1 and type-2 are human pathogens that cause primary, latent, and recurrent infections. HSV infection has various clinical manifestations including genital herpes, oral-facial infections, cutaneous and ocular infections, herpes encephalitis, neonatal herpes and erythema multiforme. HSV-1 predominantly causes herpes labialis and HSV-2 causes herpes vulvovaginitis. Genital HSV infection is a sexually transmitted disease that is prevalent worldwide and is becoming an increasingly important public health issue. There has been a 30% increase in the incidence of sexually transmitted HSV infections over the last two decades in the United States alone. Detection of HSV during pregnancy is very important since exposure of the neonate during delivery could result in infection. HSV infection is commonly treated using anti-viral agents such as acyclovir, valacyclovir or famciclovir.

Common methods of detection of HSV infection include serological testing, viral culture or polymerase chain reaction (PCR) followed by microtiter plate detection (Riley, 1998). These assays are time consuming and are not amenable to the rapid diagnosis and treatment of HSV infected individuals. An assay which is faster, less labor intensive and comparable in sensitivity to microtiter plate based assays is desirable.

SUMMARY OF THE INVENTION

The polynucleotides, kits and methods of the present invention are utilized in a qualitative PCR assay for the detection of HSV in a sample. Additionally, the assay can be performed in the presence of an internal amplification control to detect false negative results. The methods of the present invention require minimal manipulation and may be used and performed in a closed tube, thereby greatly reducing the risk of contamination and reducing the time and effort needed for the test.

The invention provides for a purified polynucleotide selected from the group consisting of SEQ ID NOS: 1–11.

The invention also provides for a pair of polynucleotide primers for a polymerase chain reaction, wherein the primers comprise SEQ ID NO:1 and SEQ ID NO:2.

The invention also provides for a polynucleotide for HSV detection, wherein said polynucleotide comprises SEQ ID NO:4.

In a preferred embodiment, the polynucleotide comprises a labeled polynucleotide.

In another embodiment, the labeled polynucleotide comprises a pair of fluorophore/quencher labels.

The invention also provides for a pair of polynucleotides for HSV detection wherein said pair of polynucleotides is selected from the group consisting of SEQ ID NO:3 and SEQ ID NO:4, and SEQ ID NO:3 and, SEQ ID NO:3.

In a preferred embodiment, the pair of polynucleotides comprises a labeled first polynucleotide and a labeled second polynucleotide, wherein the first and second polynucleotides are differentially labeled.

In another embodiment, the first and second differentially labeled polynucleotides each comprises a pair of fluorophore/quencher labels.

In another embodiment, the fluorophore label is different between said first and second polynucleotides and wherein said quencher label is the same between first and second polynucleotides.

The invention also provides for a kit for HSV detection comprising a pair of polynucleotides wherein said pair of polynucleotides is selected from the group consisting of SEQ ID NO:3 and SEQ ID NO:4, and SEQ ID NO:3 and, SEQ ID NO:3, and packaging materials therefor.

The polynucleotide primers will include a forward and a reverse primer, the forward primer being complementary to a first strand of the target nucleic acid and positioned upstream of (5' to) a region in the target sequence to be amplified, and the reverse primer will be complementary to the second strand (or the complementary strand of the first strand) and positioned downstream of (3' to) a region to be amplified.

In a preferred embodiment, the kit further comprises a pair of polynucleotide primers wherein the primers comprise SEQ ID NO: 1 and SEQ ID NO:2, and a DNA polymerase.

The invention also provides for a kit for performing a polymerase chain reaction comprising a pair of polynucleotide primers wherein the primers comprise SEQ ID NO: 1 and SEQ ID NO:2, a DNA polymerase, and packaging materials therefor.

In a preferred embodiment, the DNA polymerase is thermostable.

In another embodiment, the kit further comprises a buffer suitable for HSV detection and polymerase chain reaction.

In another embodiment, the kit further comprises an internal amplification control plasmid comprising sequences presented in SEQ ID NO:8 AND SEQ ID NO:9.

In another embodiment, the kit further comprises a first control template having a sequence presented in SEQ ID NO:6 and a second control template having a sequence presented in SEQ ID NO:7.

The invention also provides for a kit for HSV detection, comprising a polynucleotide for HSV detection having a sequence presented in SEQ ID NO:4, a pair of polynucleotides for polymerase chain reaction wherein a first polynucleotide of the pair has the sequence presented in SEQ ID NO:1 and a second polynucleotide of the pair has the sequence presented in SEQ ID NO:2, a DNA polymerase, and a buffer suitable for HSV detection and polymerase chain reaction.

In a preferred embodiment, the kit further comprises a control polynucleotide having the sequence presented in SEQ ID NO:3, and an IAC plasmid comprising sequences presented in SEQ ID NO:8 AND SEQ ID NO:9.

In another embodiment, the kit further comprises a first control template having a sequence presented in SEQ ID NO:6 and a second control template having a sequence presented in SEQ ID NO:7.

The invention also provides for a kit for HSV detection, comprising a pair of polynucleotides for HSV detection selected from the group consisting of SEQ ID NO:3 and SEQ ID NO 4, or SEQ ID NO:3 and SEQ ID NO:3, a pair of polynucleotides for polymerase chain reaction wherein a first polynucleotide of the pair for polymerase chain reaction has the sequence presented in SEQ ID NO:1 and a second polynucleotide of the pair for polymerase chain reaction has the sequence presented in SEQ ID NO:2, a DNA polymerase, and a buffer suitable for HSV detection and polymerase chain reaction.

In a preferred embodiment, the kit further comprises a control polynucleotide having the sequence presented in SEQ ID NO:3, and an IAC plasmid comprising sequences presented in SEQ ID NO:8 AND SEQ ID NO:9.

In another embodiment, the kit further comprises a first control template having the sequence presented in SEQ ID NO:6 and a second control template having the sequence presented in SEQ ID NO:7.

The invention also provides for a method for HSV detection, comprising the steps of:
  (a) contacting a target nucleic acid with a polynucleotide comprising SEQ ID NO:4, wherein the target nucleic acid comprises a sequence complementary to the polynucleotide, wherein a hybrid forms between the target nucleic acid and the polynucleotide under conditions which permit formation of said hybrid; and (b) detecting said hybrid.

In a preferred embodiment, the polynucleotide is labeled.

In another embodiment, the detecting step comprises detecting emission of fluorescence.

The invention also provides for a method for HSV detection, comprising the steps of:
  (a) mixing a target nucleic acid with a polynucleotide for detecting HSV comprising SEQ ID NO:4, and a pair of polynucleotides for polymerase chain reaction comprising SEQ ID NO:1 and SEQ ID NO:2, wherein the target nucleic acid comprises the sequence complementary to the polynucleotide for detecting HSV and a sequence complementary to the pair of polynucleotides for polymerase chain reaction; (b) incubating a mixture of step (a) under conditions which permit a polymerase chain reaction to generate a product comprising a sequence to the polynucleotide for detecting HSV and which permit formation of a hybrid between the polynucleotide for detecting HSV and said product; and (c) detecting the hybrid.

In a preferred embodiment, the polynucleotide for detecting HSV is labeled.

In another embodiment, the detecting step comprises detecting emission of fluorescence.

The invention also provides for a method for HSV detection, comprising the steps of:
  (a) contacting a target nucleic acid with a pair of polynucleotides selected from the group consisting of SEQ ID NO:3 and SEQ ID NO:4 or SEQ ID NO:3 and SEQ ID NO:3, wherein the target nucleic acid comprises a sequence complementary to at least one of said polynucleotide, wherein a hybrid forms between the target nucleic acid and at least one of the polynucleotide under conditions which permit formation of the hybrid; and (b) detecting the hybrid.

In a preferred embodiment, the polynucleotides for detecting HSV are differentially labeled.

In another embodiment, the detecting step comprises detecting emission of fluorescence.

The invention also provides for a method for HSV detection, comprising the steps of: (a) mixing a target nucleic acid with a pair of polynucleotides for detecting HSV selected from the group consisting of SEQ ID NO:3 and SEQ ID NO:4 or SEQ ID NO:3 and SEQ ID NO:3, and a pair of polynucleotides for polymerase chain reaction comprising SEQ ID NO:1 and SEQ ID NO:2, wherein the target nucleic acid comprises a sequence complementary to at least one of the polynucleotides for detecting HSV and a sequence complementary to the pair of polynucleotides for polymerase chain reaction; (b) incubating a mixture of step (a) under conditions which permit a polymerase chain reaction to generate a product comprising a sequence of at least one of the polynucleotides for detecting HSV and which permit formation of a hybrid between at least one of the polynucleotide for detecting HSV and the product; and (c) detecting the hybrid.

In a preferred embodiment, the polynucleotides for detecting HSV are differentially labeled.

In another embodiment, the detecting step comprises detecting emission of fluorescence.

Any of the kits described above may also include an internal amplification control (IAC). The internal amplification control provides a polynucleotide for hybridization to an IAC sequence, a control plasmid comprising an IAC sequence, and a control single-stranded oligonucleotide comprising an IAC sequence. Preferably, the IAC polynucleotide comprises a sequence presented in SEQ ID NO:3, the IAC plasmid comprises a double-stranded IAC sequence synthesized by the extension of overlapping polynucleotides presented by SEQ ID NO:8 and SEQ ID NO:9, and the control single-stranded oligonucleotide IAC sequence comprises a sequence presented in SEQ ID NO:5.

BRIEF DESCRIPTION OF THE DRAWINGS

FIG. 1 shows the sequences amplified by the PCR reaction for HSV-1, HSV-2 and IAC. The nucleotides in caps (T or C) indicate the sequence difference between HSV-1 and HSV-2 and the positions where the HSV-TC molecular beacon hybridizes (underlined). Other highlighted nucleotides indicate other sequence differences between HSV-1 and HSV-2. The amplification primer binding sites are italicized. The PCR products generated are 109 bp.

FIG. 4A shows the results when IAC template (0.5 pg/reaction) was evaluated with b294 (TET) and b290 (FAM). FIG. 4B shows HSV-1 viral DNA at two concentrations (5000 copies and 500 copies) used as the template with b294 (TET). FIG. 4C is the same as FIG. 4B except that HSV-2 viral DNA was used as the template. FIG. 4D shows the results when the template included 5000 copies of HSV-1+IAC (0.5 pg/reaction) or 5000 copies of HSV-2+IAC (0.5 pg/reaction) or no template (NTC) and evaluated with both b290 (FAM, IAC-specific) and b294 (TET, HSV-TC).

FIG. 5A shows the results when HSV-1 was used as a template and FIG. 5B shows the results when HSV-2 was used as a template. Both reactions contained the HSV-TC and IAC molecular beacons.

FIG. 7A shows the TET and FAM views while FIG. 7B shows the PCR products electrophoresed on a 2% agarose TBE gel.

FIG. 8A shows the TET and FAM views while FIG. 8B shows the PCR products electrophoresed on a 2% agarose TBE gel.

DETAILED DESCRIPTION OF THE INVENTION

Figure 2:
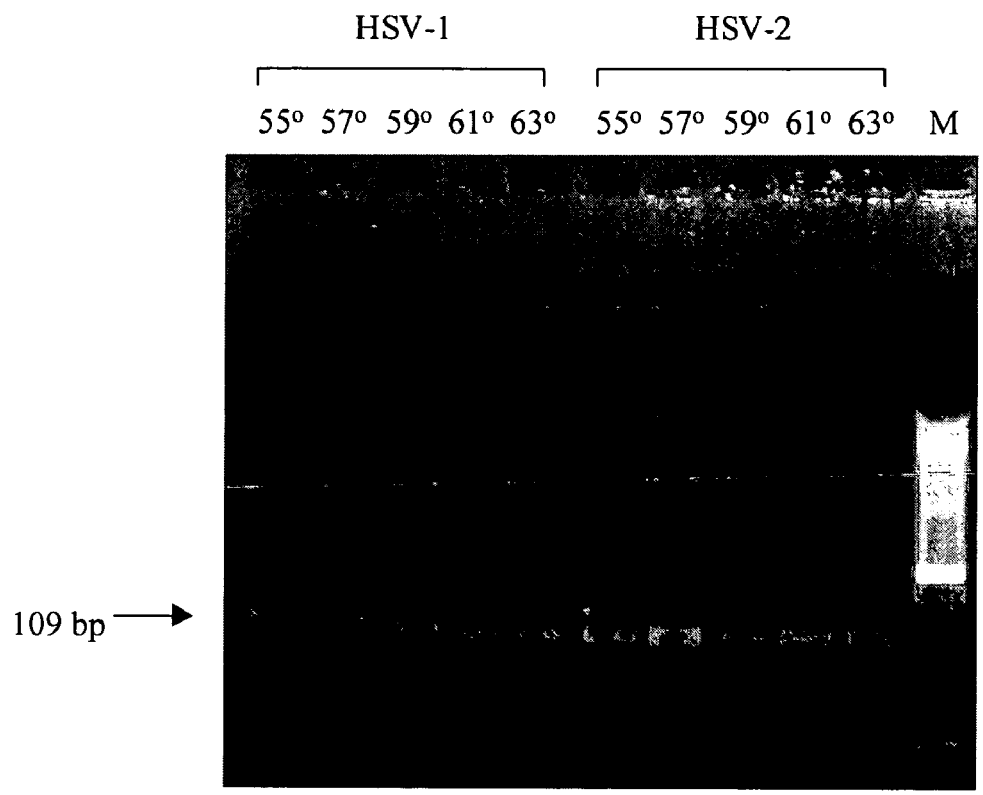
FIG. 2 is a photograph of PCR products electrophoresed on a 2% agarose TBE gel to determine the optimal annealing temperature for HSV-TC amplification. The PCR product is 109 bp and indicated with an arrow.

The present invention relates to a qualitative PCR assay for the detection of HSV strains type-1 and type-2. The present invention provides a pair of polynucleotides for polymerase chain reaction (PCR) to amplify a HSV sequence present in a sample. The present invention also provides polynucleotides, preferably labeled with a fluorophore, for detecting both HSV viral strains. More particularly, the polynucleotides for detecting HSV are molecular beacons. The present invention also provides polynucleotides, including templates and molecular beacons, for internal amplification control reactions to detect false positives and false negatives. According to the present invention, the PCR, detection for HSV, and internal amplification controls can be performed in the same reaction tube, thus reducing cost, time, and contamination. The present invention consistently allows the detection of as few as 100 copies of HSV DNA per reaction.

Definitions

As used herein, the term "polynucleotide(s)" generally refers to any polyribonucleotide or poly-deoxyribonucleotide, which may be unmodified RNA or DNA or modified RNA or DNA. "Polynucleotide(s)" include, without limitation, single- and double-stranded nucleic acids. As used herein, the term "polynucleotide(s)"also includes DNAs or RNAs as described above that contain one or more modified bases. Thus, DNAs or RNAs with backbones modified for stability or for other reasons are "polynucleotide(s)". The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "molecular beacon" as used herein are single-stranded polynucleotide probes that possess a stem-and-loop hairpin structure. The loop portion of the molecule is a probe sequence complementary to a target sequence (e.g., an internal region of a sequence amplified by PCR) and the stem is formed by short complementary sequences located at the opposite ends of the molecule. The molecule is labeled with a fluorophore at one end and a quencher at the other end. When free in solution, the stem keeps the fluorophore and the quencher in close proximity, causing the fluorescence of the fluorophore to be quenched by energy transfer. When bound to its complementary target, the probe-target hybrid forces the stem to unwind, separating the fluorophore from the quencher, and restoring the fluorescence. The hairpin stem significantly enhances the specificity of molecular beacons, enabling them to distinguish targets that differ by as little as a single nucleotide. In addition, the hairpin conformation allows a variety of fluorophores to be used in conjunction with the same quencher. Thus, more than one molecular beacon, each labeled with a different fluorophore, can be used to detect several different target sequences present in the same solution.

"HSV type common (TC)" as used herein refers generally to both HSV type-1 and type-2 strains. The HSV type-1 and type-2 strains possess significant sequence identity and therefore, a single polynucleotide or molecular beacon may be capable of hybridizing to both strains.

"HSV type specific" as used herein refers to the specific type of HSV strain being detected. Although the HSV type-1 and type-2 possess significant sequence identity, a polynucleotide or molecular beacon can be designed to hybridize to only one specific strain type, thereby allowing for discrimination between the two strains.

"Complementary" as used herein refers to the ability of a nucleic acid single strand (or portion thereof) to hybridize to an anti-parallel nucleic acid single strand (or portion thereof) by contiguous base-pairing between the nucleotides (that is not interrupted by any unpaired nucleotides) of the anti-parallel nucleic acid single strands, thereby forming a double-stranded nucleic acid between the complementary strands.

The terms "first" and "second" strand refer to the strands of a double-stranded nucleic acid, where one strand can be regarded as the first strand, and its complementary strand can be regarded as the second strand. Alternatively, the two nucleic acid strands of the double-stranded nucleic acid may be referred to as the 5' to 3' strand and its complement, the 3' to 5' strand.

As used herein, "positive" or "sense" strand refers to the strand of the DNA duplex of a gene that contains the sequence of the corresponding mRNA transcript of the gene.

"Negative strand" or "antisense" strand refers to the strand of the DNA duplex of a gene that contains the sequence that is complementary to the corresponding mRNA transcript of the gene.

A "target" nucleic acid or sample as used herein refers to the nucleic acid used for analysis and to which a polynucleotide for HSV detection or for an internal amplification control and/or a pair of PCR primers is hybridized in order to ascertain the presence or absence of the nucleic acid.

As used herein, "forward amplification primer" refers to a polynucleotide used for PCR amplification that is complementary to the sense strand of the target nucleic acid. "Reverse amplification primer" refers to a polynucleotide used for PCR amplification that is complementary to the antisense strand of the target nucleic acid. For a given target, a forward and reverse amplification primer are used to amplify the DNA in PCR.

As used herein, "oligonucleotide primers" refer to single-stranded DNA or RNA molecules that are capable of hybridizing to a nucleic acid template and are capable of priming (or initiating) enzymatic synthesis of a second nucleic acid strand.

As used herein, "amplifying" refers to producing additional copies of a nucleic acid sequence, preferably by the method of polymerase chain reaction (Mullis and Faloona, 1987, *Methods Enzymol.*, 155:335).

"PCR product" as used herein refers to the nucleic acid generated from PCR amplification of a given region of a target nucleic acid.

"Hybrid" as used herein refers to a double-stranded nucleic acid, or a region having a double-stranded nucleic acid, in which the first and second strands of the nucleic acid are complementary to each other.

A "sample" as used herein refers to a target nucleic acid, and may consist of purified or isolated nucleic acid, or may comprise a biological sample such as a tissue sample, a biological fluid sample, a cell sample containing a nucleic acid.

"Template" as used herein refers to a nucleic acid sequence that encompasses the region of the target sequence to which the polynucleotides and primers are complementary.

"Control DNA template" in general as used herein refers to the sequence-matched targets useful in the invention.

"Internal amplification control" or "IAC" as used herein serves to detect false negatives and/or false positives in the assay for HSV detection. The IAC comprises a control plasmid that contains sequences capable of being amplified by the same PCR primers as those used for HSV sequence amplification and sequences to which a polynucleotide or molecular beacon is capable of hybridizing but to which a polynucleotide or molecular beacon for HSV detection cannot bind, and a control single-stranded polynucleotide target to which the IAC molecular beacon can hybridize.

Polynucleotides

All polynucleotides, including PCR amplification primers and single-stranded molecular beacon targets, were custom synthesized at BioCrest (Bastrop, Tex.). Molecular beacons were custom synthesized and purified at Midland Certified Reagent Company (Midland, Tex.). PCR primer design and target hybridization temperature estimations were based on the HSV type-1 and type-2 nucleic acid sequence and aided by the Oligo 5.0 program for a PC (MBI, Cascade, Colo.). Molecular beacon folding patterns and stem melting temperatures were approximated by a folding program provided by Washington University, St. Louis, Mo. (http://mfold1.wustl.edu/~mfold/dna/form1.cgi).

Design of Molecular Beacons for HSV Detection, HSV Type Discrimination and IAC

The present invention allows the simultaneous use of two molecular beacons in the same reaction. The molecular beacons can differ only by a single nucleotide, therefore not only enabling the detection of HSV generally in a sample but also enabling the discrimination of the specific HSV type in the sample. It also definitively discriminates a true negative result from a false negative result that is due to PCR failure by the use of an internal amplification control in the same reaction. Therefore, the molecular beacons of the present invention are particularly suitable as hybridization probes for HSV detection and for HSV type discrimination.

For detection of HSV, a single region which could be used for both a type common (TC) and a type specific assay is selected. In other words, a region which contains both identity and variation between the two viral types is desirable. After comparing a number of type 1 and type 2 genomes, a region within the gB gene is selected. The gB region contains a number of nucleotide differences between the two types (all C to G changes), but also contains a single T to C polymorphism (FIG. 1). HSV-1 contains a C and HSV-2 contains a T base. The molecular beacon for the type common assay (HSV-TC molecular beacon) is centered on that T/C nucleotide and used the universal K base at that location within the beacon (Table 1). The K base has been shown to hybridize with either a T or a C (Hill, et al., 1998a and Hill, et al., 1998b), and therefore allows for the detection of either viral type.

For discrimination between HSV type-1 and type-2, the same region is used for molecular beacons containing either a T or a C to differentiate between the viral types (Table 1).

The IAC sequence is simply a region of the HSV sequence but in the opposite orientation. An IAC sequence encompasses the same amplification primer binding sites as those used to amplify the HSV sequence. The IAC-specific molecular beacon is shown in Table 1. Both the HSV molecular beacons and IAC-specific molecular beacons hybridize to the sense strand.

As described, the present invention allows simultaneous use of more than one molecular beacon. When more than one molecular beacon is used, they are preferably labeled with different fluorophores that emit fluorescent light at specific optical wavelengths. For example, the HSV-TC molecular beacon can be simultaneously used with the IAC molecular beacon. As a result, detection of HSV can be carried out in the same PCR reaction as a control reaction. In most cases, the fluorophore TET (Tetrachloro-fluorescein) is used to label the HSV molecular beacons and FAM (6-carboxy-fluorescein) is used to label the IAC-specific beacon. When discriminating between HSV types in the same reaction, the HSV molecular beacon specific for one type may be labeled with TET while the HSV molecular beacon specific for the other HSV type is labeled with FAM. The two fluorescent signals can be distinguished by using the ABI7700 sequence detector software. DABCYL is used as the quencher for all of the molecular beacons. Table 1 lists the sequences of the molecular beacons used in the kits. These beacons are dissolved in TE buffer (10 mM Tris and 1 mM EDTA, pH 8.0) and stored at −20° C. The concentrations of all the beacons are determined by UV absorbance (260 nm) using a spectrophotometer (Beckman DU600).

TABLE 1

| SEQ ID NO | POLYNUCLEOTIDE | SEQUENCE |
| --- | --- | --- |
| 1 | Forward PCR primer | 5'-tca cca ccg tca gca cct tc -3' |
| 2 | Reverse PCR primer | 5'-agc agg ccg ctg tcc ttg -3' |
| 3 | IAC specific molecular beacon | 5'-ccctgc gtagtggtacgacctcct gcaggg -3' |
| 4 | HSV type common (TC) molecular beacon | 5'-ccctgca aactcgtgKtcctccagca tgcaggg -3' |
| 5 | ssOligonucleotide target for IAC specific molecular beacon | 5'-agc act agg agg tcg tac cac tac aac tcc -3' |
| 6 | ssOligonucleotide molecular beacon target for HSV type-1 | 5'-aac atc acc atg ctg gag gaT cac gag ttt gtc ccc ctg -3' |
| 7 | SsOligonucleotide molecular beacon target for HSV type-2 | 5'-aac atc acc atg ctg gag gaC cac gag ttt gtc ccc ctg -3' |
| 8 | Forward primer for synthesis of IAC | 5'-atcgaattctcaccaccgtcagcaccttctagagcaccgcccacatgtggaggt ccccctgtttgagcactagg -3' |
| 9 | Reverse primer for synthesis of IAC | 5'- atcgaattcagcaggccgctgtccttgtagctggagttgtagtggtacgacct cctagtgctcaaacagggg -3' |

TABLE 1-continued

| SEQ ID NO | POLYNUCLEOTIDE | SEQUENCE |
| --- | --- | --- |
| 10 | HSV-1 type specific molecular beacon | 5'-ccctgca aactcgtgTtcctccagca tgcaggg -3' |
| 11 | HSV-2 type specific molecular beacon | 5'-ccctgca aactcgtgCtcctccagca tgcaggg -3' |

Internal Amplification Control (IAC) Plasmid

An internal amplification control is needed in PCR-based assays where human samples (e.g. cerebrospinal fluid (CSF)) usually have a high probability of containing inhibitors. The internal amplification control (IAC) for the HSV assay is generated by overlap extension of two oligonucleotides, each of which contains one of the PCR amplification primer binding regions (see Table 1). Additionally, EcoRI sites are placed 5' on each extension oligo in order to facilitate cloning. The extension is performed with Pfuturbo using the following extension profile: 95° C. for 15 sec (1x), followed by 60° C. for 40 sec (40x). The product is gel purified, EtOH precipitated, digested with EcoRI and cloned into pBluescript. The plasmid is sequenced to verify that the product contained the IAC sequence.

Assay for HSV Detection

The present invention provides a pair of polynucleotides for polymerase chain reaction (PCR) to amplify a HSV sequence present in a sample. The present invention also provides molecular beacons for detecting both HSV type-1 and type-2 viral strains. The present invention further provides polynucleotides, including templates and molecular beacons, for internal amplification control reactions to detect false positive and false negative results.

Ideally, the PCR primers and molecular beacons hybridize to their template at the same annealing temperatures so that the PCR and detection reactions can be performed in the same tube under the same PCR conditions. Upon amplification of the template present in a sample, the molecular beacon hybridizes to the amplified sequence and fluoresces. The fluorescence is detected and is a measure of the quantity of HSV template present in the sample.

Presence of a target or template in the sample is detected by converting the emitted fluorescent signal into a threshold cycle (Ct) value. Threshold cycle is the PCR cycle at which the fluorescent signal is first detected above background. The Ct values are obtained by analyzing the fluorescence data using the ABI7700 sequence detection software. The amount of target or template in a sample can be determined by plotting the Ct value generated by the known quantities of a target or template against the Ct value generated by the sample using the same molecular beacons. In the current study, Ct values of 38–40 (40 is the maximum PCR cycle number used) indicate the absence of a specific target or template in a sample. Ct values ranging from 20–30 indicate the presence of a specific target or template in a sample.

Kits

Kits according to the present invention may thus include a pair of molecular beacons (a molecular beacon for HSV-TC and another for IAC) and/or a pair of PCR primers having sequences disclosed herein. Optionally, a kit useful according to the invention may also contain one or more of an HSV type specific molecular beacon which will recognize a specific HSV type but not the other. The kit according to the invention may also contain dNTPs, a DNA polymerase, for example, the Taq2000 DNA polymerase, and a PCR buffer.

The following Examples are intended to illustrate the present invention, but are not intended to be limiting in any manner.

EXAMPLE 1

Optimization of PCR Amplification Conditions

Optimal PCR conditions were determined using the amplification primers with either the HSV type-1 or HSV type-2 genomic DNA (10,000 copies/rxn) purchased as viral stocks from Advanced Biotechnologies Incorporated (Columbia, Md.). The viral stocks were diluted in HSV negative cerebrospinal fluid (CSF) and stored at –80° C. HSV-negative cerebrospinal fluid (CSF) was obtained from Cenetron Diagnostics by pooling normal patient samples. The PCR buffer used was the molecular beacons core buffer (1x=70 mM Tris-HCl (pH8.5), 40 mM KCl and 0.1% Tween20). PCR annealing temperature optimization was initially determined using the gradient feature of the RoboCycler 96 (Stratagene). The RoboCycler gradient PCR profile was: 95° C. for 3 min (1x) followed by 95° C. for 15 sec, 55° C.–63° C. gradient for 30 sec, then 72° C. for 30 sec (40x) and concluded with a final extension of 72° C. for 5 min (1x). The resulting PCR products were fractionated on 2% (1x TBE) agarose gels and optimal conditions were determined.

FIG. 2 shows that amplification proceeds well at temperatures between 55° C. and 63° C. Additionally, non-specific amplification products were not detected within that annealing range.

EXAMPLE 2

Melting Curve Analysis

A melting curve analysis is carried out by incubating a molecular beacon with or without its complementary single stranded oligonucleotide target. Molecular beacon melting curve analysis was performed to determine if the HSV molecular beacons are capable of hybridizing to the correct targets at the amplification annealing temperature. For the HSV type common specific beacon (containing the K base), two single-stranded (ss) oligonucleotide targets were evaluated. One ss oligo target contained the HSV type 1 sequence (containing a C base), while the other contained HSV type 2 sequence (containing a T base). For the IAC specific molecular beacon, a single ss oligo target was tested. The single stranded oligonucleotide targets (HSV-1, HSV-2, and IAC) are listed in Table 1.

Figure 3:
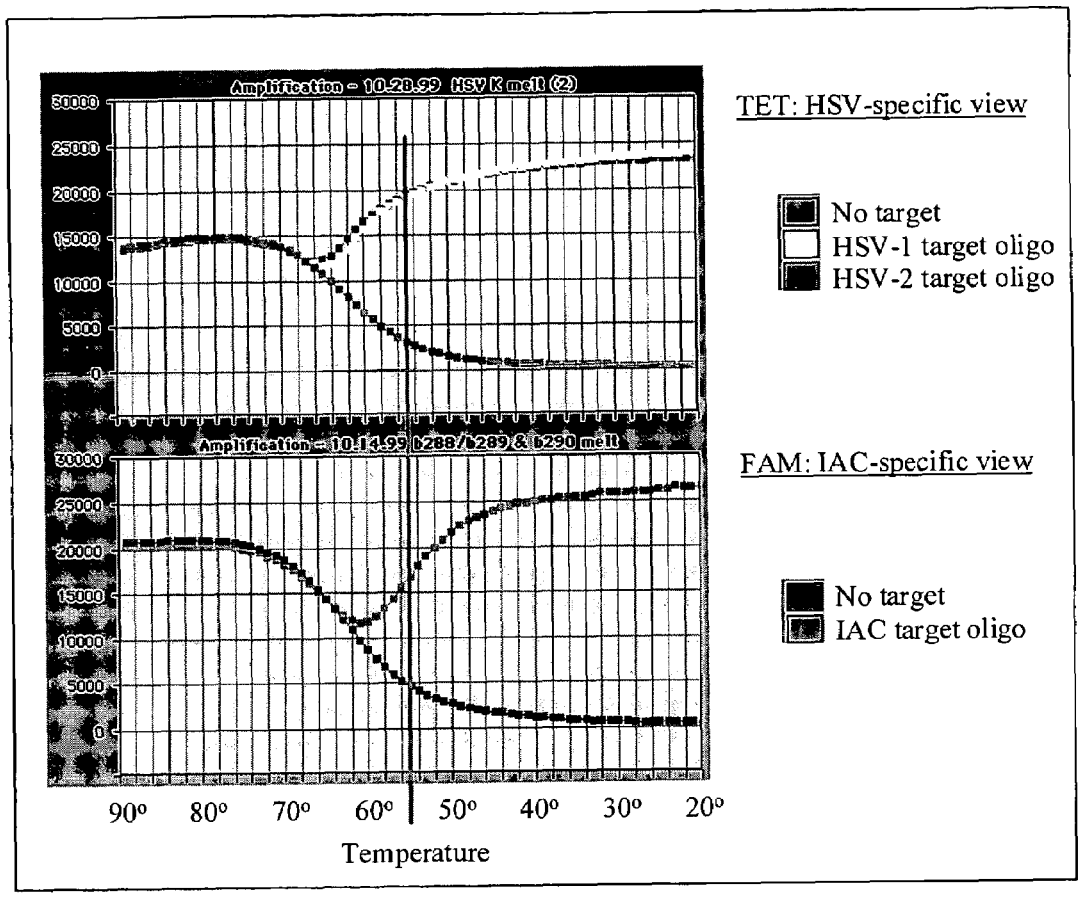
FIG. 3 shows melting curves of the HSV-TC and IAC specific molecular beacons.

FIG. 3 shows the melting curve analysis for the HSV-TC specific and IAC specific molecular beacons. The analysis of each beacon was performed in 1xPCR buffer from 90° C. to 20° C., decreasing 1° C./cycle (1 minute). A potential annealing temperature of 55° C. is indicated. The data show that at 55° C., both the HSV-TC specific and IAC-specific molecular beacons form thermally stable complexes with their respective targets, as indicated by the increase in reporter dye fluorescence compared to the fluorescence generated without target present. Also, the HSV-TC specific molecular beacon shows no differential hybridization between the HSV-1 and HSV-2 ss oligos, indicating the potential to detect either viral template.

EXAMPLE 3

PCR-Molecular Beacon Assay for Detection of HSV Using HSV Genomic DNA

PCR and detection of HSV genomic DNA and IAC plasmid DNA was performed using the ABI7000. Table 2 shows the PCR conditions used for the amplification and detection of templates. The overall time required for performing the HSV type common assay is 2 hours and 15 minutes using a three-step amplification profile.

TABLE 2

| Components | Volume Added | Final Concentration |
|---|---|---|
| PCR buffer (10X) | 5 µL | 1X[a] |
| dNTPs (20 mM, 5 mM each) | 0.5 µL | 200 nM |
| Primer mix (20 µM, 10 µM each) | 2 µL | 800 Nm |
| Molecular beacons (MB) mix (10 µM)[b] | 2 µL | 400 nM[c] |
| Taq2000 (5 U/µL) | 0.5 µL | 0.05 U/µL |
| Template | variable[d] | variable |
| dH$_2$O to total volume of 50 µL | | |

AB17700 Amplification Profile:

| Profile A: | 1 cycle | 95° C. - 10 min |
| | 40 cycles | 95° C. - 30 sec/55° C. - 30 sec/72° - 30 sec |
| Profile B: | 1 cycle | 95° C. - 3 min |
| | 40 cycles | 95° C. - 30 sec/55° C. - 30 sec/72° - 30 sec |

Figure 4:
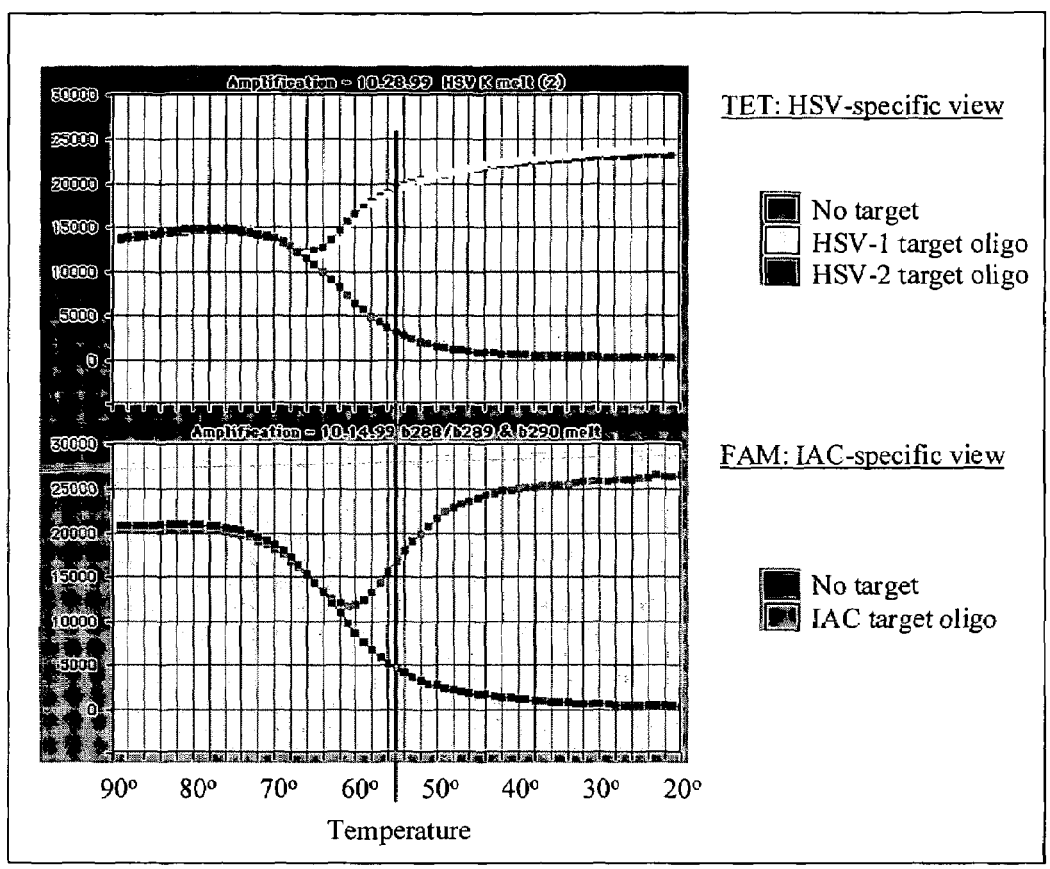
FIG. 4 shows the results of a PCR analysis using the molecular beacon 290 (FAM) for IAC and molecular beacon 294 (TET) for HSV-TC.
Figure 4:
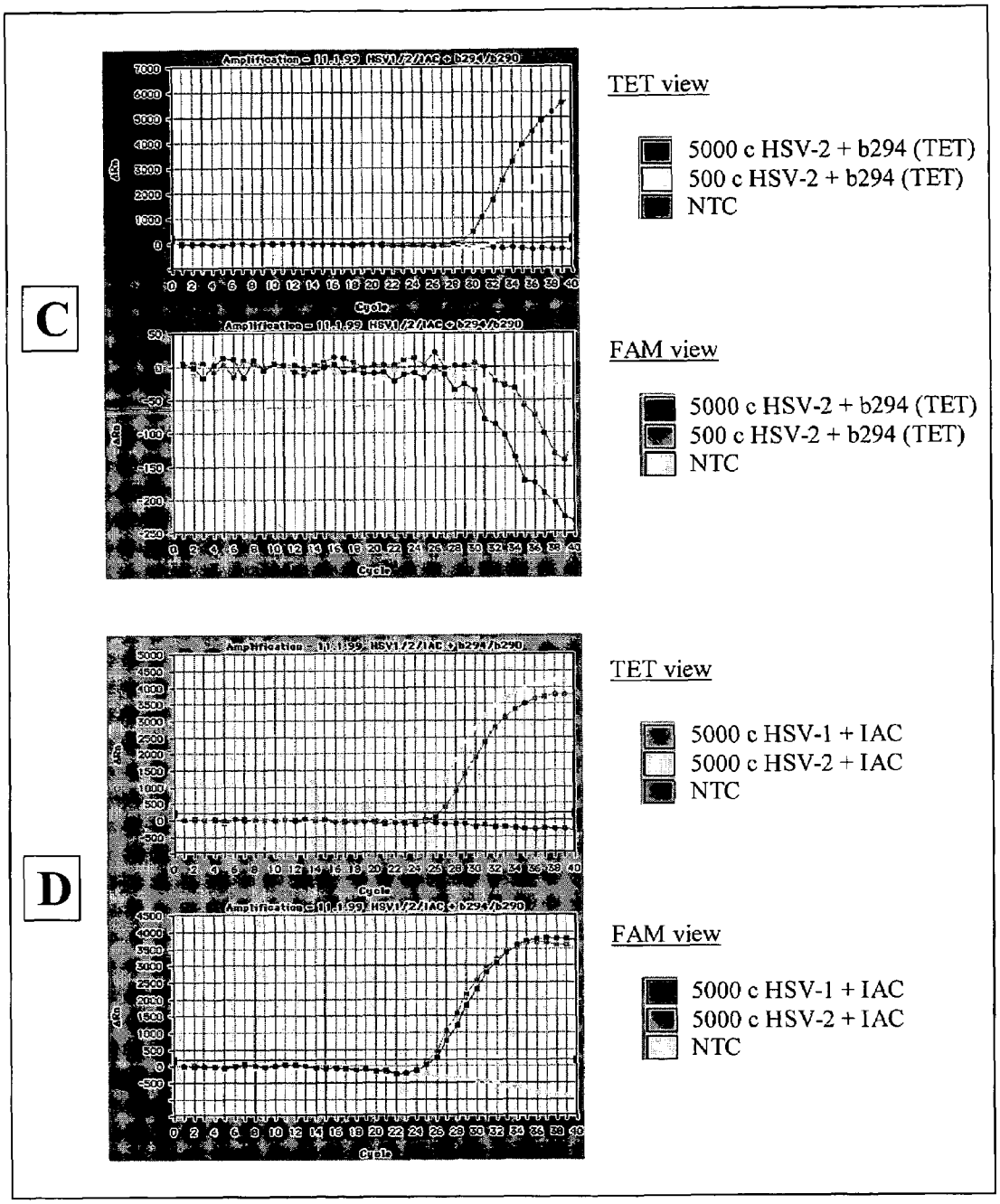

[a]1X = core buffer
[b]5 µM FAM-labeled IAC MB + 5 µM TET-labeled HSV type common (TC) MB
[c]FAM-labeled IAC MB (200 nM) + TET-labeled HSV MB (200 nM)
[d]HSV genomic DNA = 0–5000 copies per reaction
IAC plasmid DNA control = 0–5 pg per reaction Using the above conditions, the molecular beacons were individually examined for specific hybridization to their respective targets. The molecular beacon specific for IAC, b290, is labeled with FAM. The molecular beacon specific for HSV-TC, b294, is labeled with TET. Two identical PCR reactions, with the exception of the molecular beacon used, containing IAC as template were evaluated (FIG. 4A). The results show that only b290 (FAM) shows any increase in signal due to amplification of IAC. The b294, specific to the HSV-TC sequence, showed no hybridization. Both reactions showed strong amplification product bands on a gel (data not shown), indicating that the amplification was successful. Similarly, reactions containing only HSV genomic DNA (type-1 or type-2) showed the opposite hybridization pattern. Only b294 showed an increase in signal with the generation of HSV-specific amplification (data not shown).

Additionally, two concentrations of HSV-1 and HSV-2 genomic DNA were evaluated in both the TET and FAM layers for specificity. FIG. 4B shows the results for HSV-1, while FIG. 4C shows the results for HSV-2. The data show that (1) a single molecular beacon with the incorporated K base will hybridize to either target with the same efficiency and (2) the associated increase in fluorescent signal is only seen in the TET view (i.e., no signal in the FAM view).

Lastly, FIG. 4D shows two multiplex reactions, one containing HSV-1 genomic DNA+IAC plasmid as templates and the other containing HSV-2 genomic DNA+IAC plasmid as templates, and a no template control (NTC). All three reactions contained both molecular beacons (b290=IAC specific and b294=HSV-TC specific). The amplification plots show increases in both the FAM and TET views indicating the presence of both templates. This was the first demonstration that multiplexes reactions for the simultaneous detection of herpes simplex (either type) and the internal amplification control would work.

Likewise, HSV type specific molecular beacons representing SEQ ID NO: 10 and SEQ ID NO: 11 can also be used in the same reaction in order to verify which type of HSV is present in the sample. For example, two reactions can be set up, one containing HSV-1 genomic DNA and, in another tube, HSV-2 genomic DNA wherein both tubes contain both type specific molecular beacons. The molecular beacons are preferably differentially labeled, for example, HSV-1 type specific beacon is labeled with TET and HSV-2 type specific beacon is labeled with FAM. In this example, the amplification plots would show a TET signal if HSV type-1 is present in the sample and a FAM signal if HSV type-2 is present in the sample. In this manner, this method can be used for the discrimination of HSV strain types.

Alternatively, the HSV type specific molecular beacons can be used separately but simultaneously with IAC. For example, HSV type-1 specific molecular beacon can be used with the IAC in the same reaction in one tube and the HSV type-2 specific molecular beacon can be used with the IAC in a separate reaction in another tube. In this embodiment, the HSV type specific molecular beacons are preferably differentially labeled from the IAC specific molecular beacon. For example, both the HSV type-1 and type-2 molecular beacons can be labeled with TET while the IAC specific molecular beacon is labeled with FAM. If a specific HSV type is present in a sample, one tube will emit TET while the other tube will not emit TET. If both tubes contain an IAC plasmid, both tubes should emit FAM if the reaction has proceeded properly. This method can be used as an alternative method for discriminating between HSV strain types.

EXAMPLE 4

Sensitivity of HSV-TC (K Base) Molecular Beacon

Figure 5:
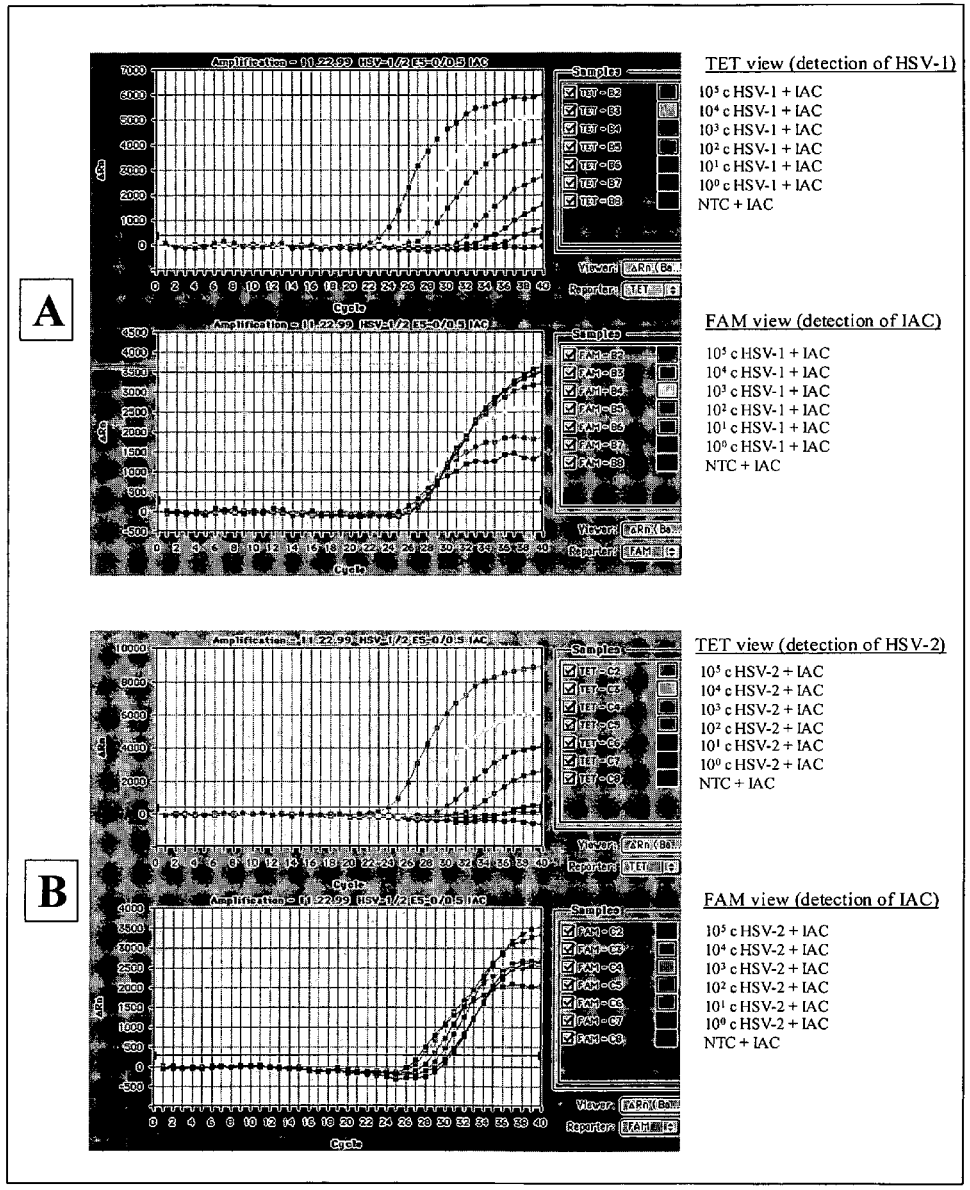
FIG. 5 shows the results of a PCR analysis used to determine the sensitivity of the HSV-TC molecular beacon.

The sensitivity of HSV detection was compared between the PCR assay of the present invention and the standard microtiter plate assay. Both assays used dilutions of HSV-1 and HSV-2 obtained from commercial HSV DNA standards (ABI, Inc., Columbia, Md.). Serial dilutions of HSV-1 and HSV-2 ($10^5$ copies to $10^0$ copies per reaction) were tested with the HSV-TC molecular beacon. FIG. 5 shows that both HSV-1 (panel A) and HSV-2 (panel B) are easily detected down to 100 copies/reaction. Greater sensitivity is often seen, such as the $10^1$ and $10^0$ samples of HSV-1 in this data. However, the reliable detection limit for this assay is 100 copies per reaction of either HSV-1 or HSV-2.

The HSV-1 and HSV-2 serial dilutions were additionally tested using a standard microtiter plate assay format (Cenetron Diagnostics SOP 6000.1) for the detection of HSV and an internal control (called ICC for internal control cassette, WalkerPeach and DuBois, patent pending). Table 3 shows the comparison of the data from the two assay formats. The PCR assay of the present invention, using HSV-1 as template, appears 5× more sensitive than the plate-based assay, whereas a greater difference is seen when using HSV-2 as template (5× to 50× more sensitive than plate-based assay).

TABLE 3

| | MICROTITER PLATE ASSAY | | | | REAL-TIME MULTIPLEX ASSAY | | |
|---|---|---|---|---|---|---|---|
| Sample | Dilution (copies/rxn) | OD405 (HSV) | OD405 (ICC) | Result | Ct (Tet-HSV) | Ct (Fam-IAC) | Result |
| HSV-1 | $10^5$ | 2.97 | 1.55 | Positive | 23.20 | 26.79 | Positive |
| HSV-1 | $10^4$ | 2.35 | 1.36 | Positive | 25.94 | 27.24 | Positive |
| HSV-1 | $10^3$ | 0.80 | 1.31 | Positive | 27.74 | 26.75 | Positive |
| HSV-1 | $10^2$ | 0.20 | 1.84 | Negative | 32.05 | 27.50 | Positive |
| HSV-1 | $10^1$ | 0.18 | 1.29 | Negative | 34.63 | 27.81 | Negative |
| HSV-2 | $10^5$ | 2.60 | 1.13 | Positive | 23.94 | 27.37 | Positive |
| HSV-2 | $10^4$ | 1.65 | 1.08 | Positive | 27.16 | 27.76 | Positive |
| HSV-2 | $10^3$ | 0.27 | 1.32 | Negative | 29.82 | 28.45 | Positive |
| HSV-2 | $10^2$ | 0.23 | 1.81 | Negative | 32.85 | 28.81 | Positive |
| HSV-2 | $10^1$ | 0.18 | 1.60 | Negative | 37.85 | 29.48 | Negative |
| NTC | — | 0.16 | 2.11 | Negative | 40.00 | 27.50 | Negative |

EXAMPLE 5

HSV Detection in Clinical Samples

Ten (10) CSF specimens (HSV status unknown) were evaluated with the PCR-molecular beacon assay. The CSF specimens were prepared by three methods (1) Cenetron Diagnostics SOP 6000.1, (2) Qiagen blood kit as modified for CSF and (3) no preparation (i.e. direct incubation with master mix). The data are not shown for preparation (1) and (2), due to failure of amplification and/or detection. It is hypothesized that in the case of (1), the concentrations of detergent (NP-40) and reducing agent (DTT) caused the inhibition of detection (bands seen on a gel). In the case of (2), it is believed that after the isolation procedure was completed, none or very little, of the HSV DNA remained, thereby causing a failure in amplification (no bands seen on gel). The third method of 'no preparation' of the specimens gave the best data and can be seen in FIG. 6.

The 10 'no prep' samples were run along side two positive controls ($10^5$ and $10^2$ copies of HSV-1 per reaction) and a negative (CSF). Specimens 2, 3, 5, 6, 9 and 10 were negative. Three specimens were positive, (4 and 8 (roughly $10^5$ copies/mL of CSF)), followed by specimen 1 (approximately $10^4$ copies/mL CSF). Specimen 7 gave a Ct value of 38 indicating a very low positive (<$10^2$ copies/mL of CSF). The results were in 100% concordance with the results performed at Cenetron Diagnostics using a microtiter-based detection system.

Figure 6:
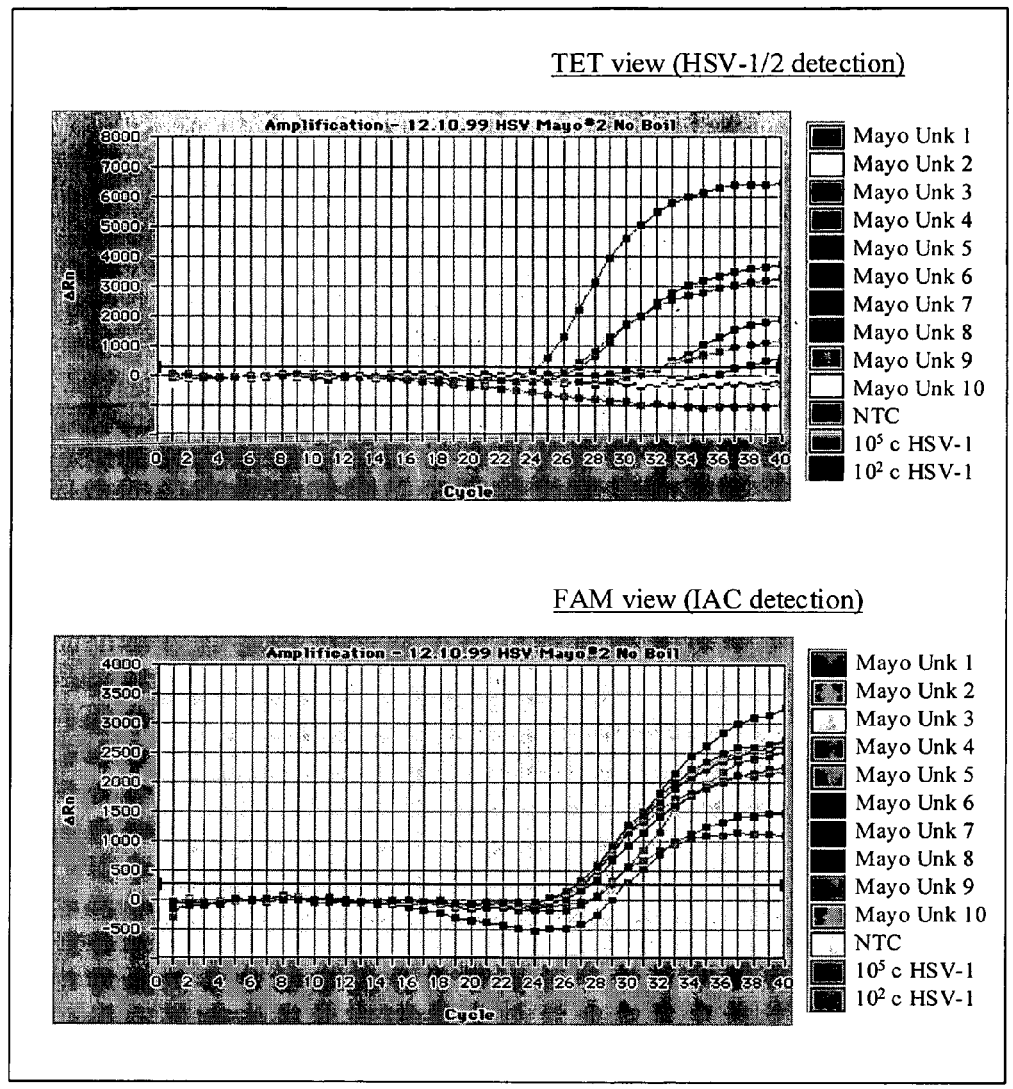
FIG. 6 shows the results of clinical samples using the PCR-molecular beacon assay of the present invention.

Although the 'no prep' method significantly reduces pre-amplification manipulation steps, the level of Ct variation in the clinical samples obtained for IAC is fairly high (FIG. 6, lower amplification plot). This variation is likely attributed to the normal variation of amplification inhibitors, protein, heme and other components found in individual patient CSF specimens. This illustrates the importance for an IAC in the master mix to detect false positives and false negatives.

To eliminate the variation associated with IAC, a second 'no prep' method was evaluated and compared. As discussed above, the methodology for clinical specimen preparation involves directly adding 25 µL of CSF to 25 µL of master mix (herein after "Method 3"). In this second 'no prep' method (herein after "Method 3A"), the amplification profile was preceded by an incubation step of 95° C. for 10 min in the thermocycler. During the incubation, the HSV capsid structure, as well as other proteins found in the CSF, is most likely to become disassociated thereby exposing the template DNA to the amplification process.

Figure 7:
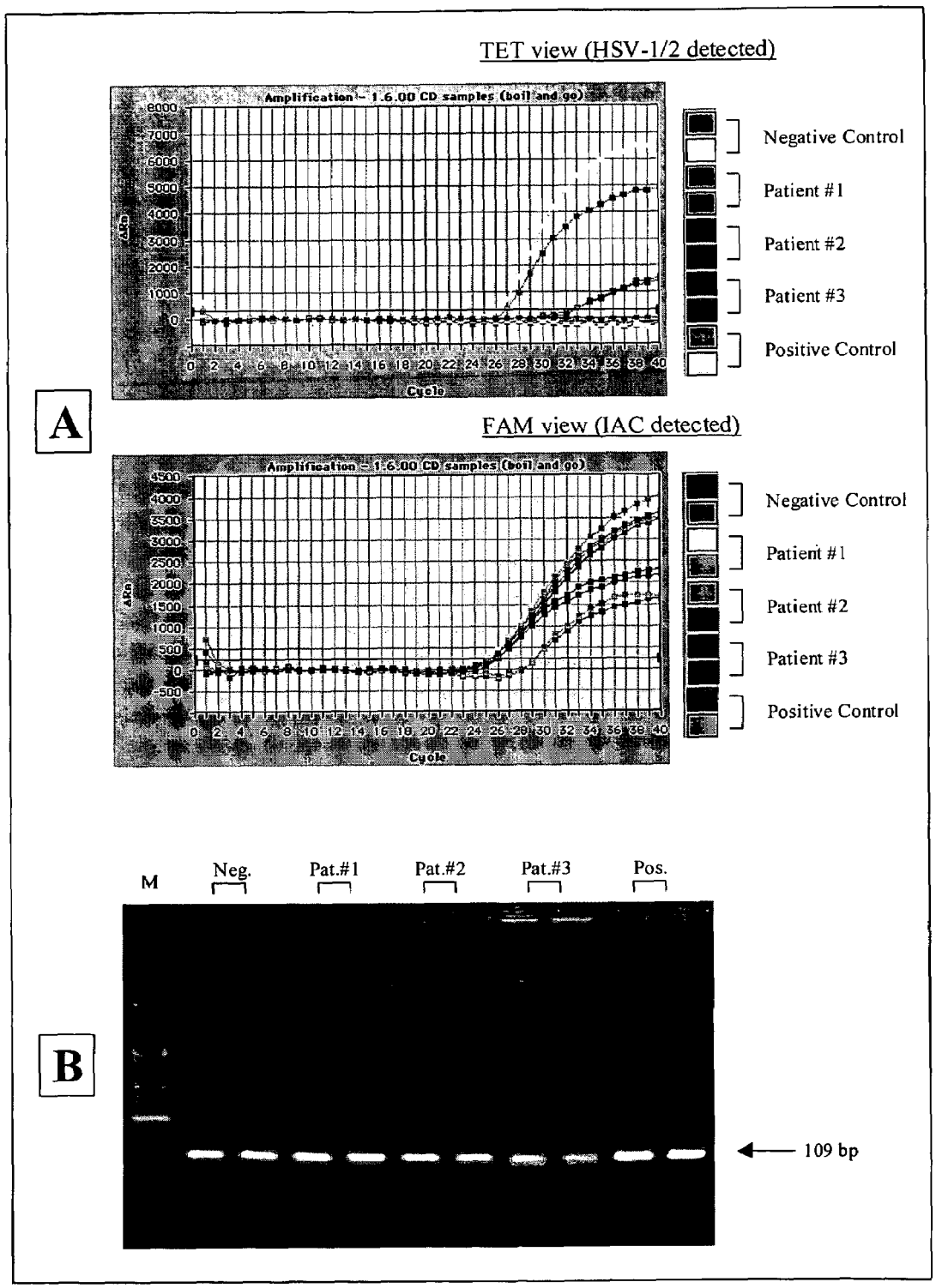
FIG. 7 shows the results of the PCR-molecular beacon assay using CSF specimens when Method 3 is employed for the preparation of the specimens.
Figure 8:
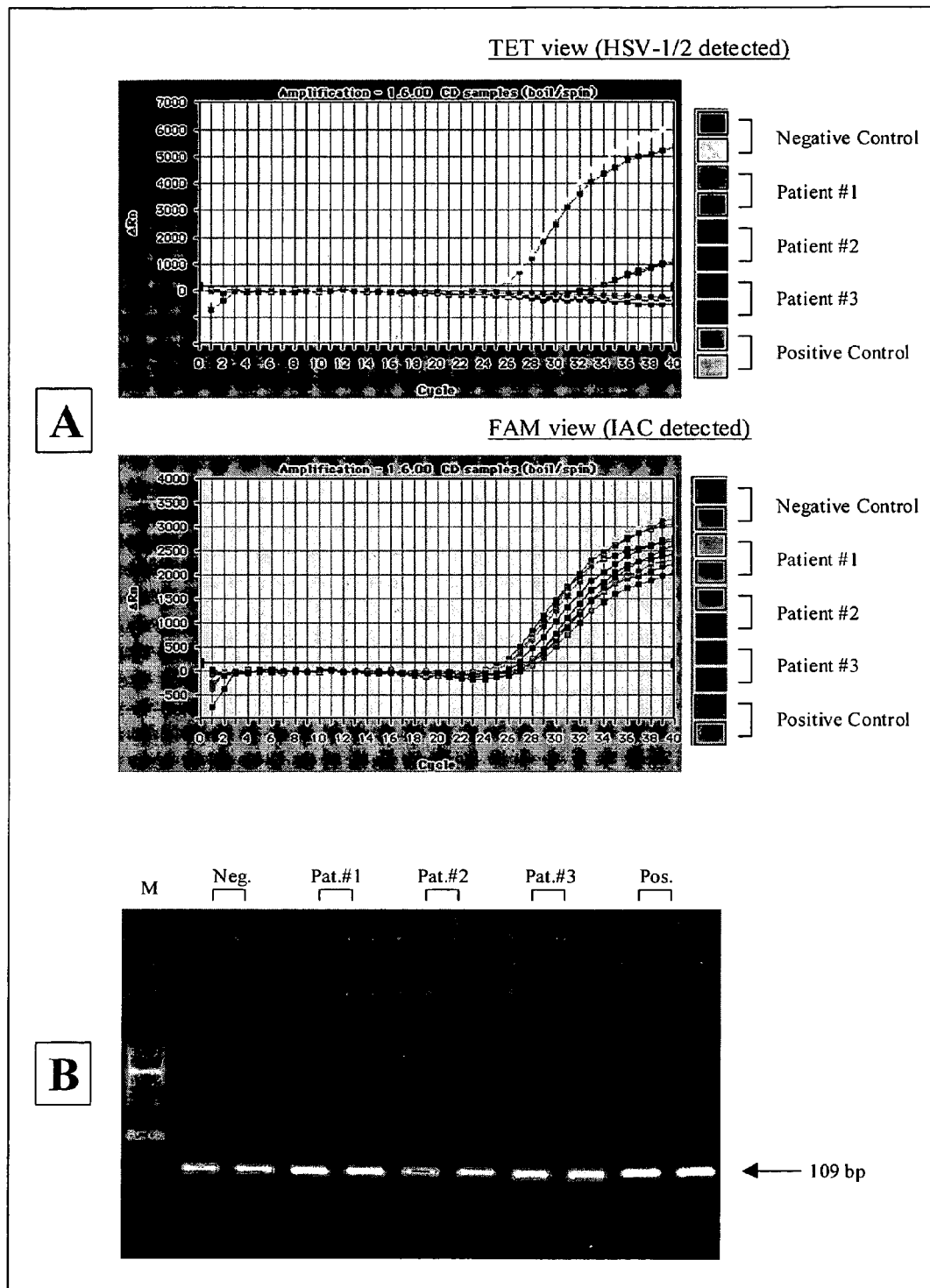
FIG. 8 shows the results of the PCR-molecular beacon assay using CSF specimens when Method 3A is employed for the preparation of the specimens. The samples used are the same as those used in FIG. 7.

Three CSF patient samples were obtained from Cenetron Diagnostics (Cedar Creek, Tex.) that allowed duplicate samples to be run in two separate experiments. Two of the specimens were negative on the microtiter plate assay, while the third was positive (data not shown). These specimens were used to compare Method 3 with Method 3A. Results using Method 3 are shown in FIG. 7. In Method 3A, 35 µL of each specimen to be tested was heated to 95° C. for 10–15 min, centrifuged and then a 25 µL aliquot was removed and added to the master mix (FIG. 8), followed by the PCR-molecular beacon assay of the present invention. Method 3A shows less variability in the IAC, suggesting that the pre-incubation step can also reduce variability in detection of HSV.

Following the initial HSV detection in the samples, the samples can be further tested for determination of which type of HSV is present in the sample. HSV type discrimination can be carried out by either using the HSV type specific molecular beacons separately or by simultaneously using both HSV type specific molecular beacons in the same reaction as described in Example 4.

EXAMPLE 6

Kits for HSV Detection

Examples of kits useful for approximately 100 reactions are shown in Tables 4–7.

TABLE 4[a]

| Material | Quantity |
|---|---|
| 10X PCR buffer[b] | 500 µL |
| 20 mM dNTPs[c] | 50 µL |
| 30 µM molecular beacons mix[d] | 175 µL |
| 40 µM primer mix[e] | 300 µL |
| 5 U/µL Taq2000 | 50 µL |
| HSV Type-specific controls[f]: | |
| HSV Type-1 ($10^5$ copies/rxn) | 250 µL |
| HSV Type-1 ($10^2$ copies/rxn) | 250 µL |
| HSV Type-2 ($10^5$ copies/rxn) | 250 µL |
| HSV Type-2 ($10^2$ copies/rxn) | 250 µL |

[a]Components for 100 assays per kit (50 uL per assay reaction volume) includes 40 type-specific control reactions
[b]10X = Core buffer (700 mM Tris, 400 mM KCl, 1% Tween) + 30 mM MgCl$_2$ (pH 8.5)
[c]5 mM each dNTP
[d]20 µM FAM-labeled IAC-specific MB + 10 µM TET-labeled HSV-TC MB
[e]20 µM each primer + IAC plasmid (83.3 pg/mL, 75,000 copies/rxn)
[f]$10^5$ = 4000 copies/µL, $10^2$ = 4 copies/µL

TABLE 5[a]

| Material | Quantity |
|---|---|
| 10X PCR buffer[b] | 500 μL |
| 20 mM dNTPs[c] | 50 μL |
| 30 μM molecular beacons mix[d] | 175 μL |
| 40 μM primer mix[e] | 300 μL |
| 5 U/μL Taq2000 | 50 μL |
| HSV Type-specific controls[f]: | |
| HSV Type-1 ($10^5$ copies/rxn) | 250 μL |
| HSV Type-1 ($10^2$ copies/rxn) | 250 μL |
| HSV Type-2 ($10^5$ copies/rxn) | 250 μL |
| HSV Type-2 ($10^2$ copies/rxn) | 250 μL |

[a]Components for 100 assays per kit (50 uL per assay reaction volume) includes 40 type-specific control reactions
[b]10X = Core buffer (700 mM Tris, 400 mM KCl, 1% Tween) + 30 mM $MgCl_2$ (pH 8.5)
[c]5 mM each dNTP
[d]20 μM FAM-labeled IAC-specific MB + 10 μM TET-labeled HSV type-1 specific MB
[e]20 μM each primer + IAC plasmid (83.3 pg/mL, 75,000 copies/rxn)
[f]$10^5$ = 4000 copies/μL, $10^2$ = 4 copies/μL

TABLE 6

| Material | Quantity |
|---|---|
| 10X PCR buffer[b] | 500 μL |
| 20 mM dNTPs[c] | 50 μL |
| 30 μM molecular beacons mix[d] | 175 μL |
| 40 μM primer mix[e] | 300 μL |
| 5 U/μL Taq2000 | 50 μL |
| HSV Type-specific controls[f]: | |
| HSV Type-1 ($10^5$ copies/rxn) | 250 μL |
| HSV Type-1 ($10^2$ copies/rxn) | 250 μL |
| HSV Type-2 ($10^5$ copies/rxn) | 250 μL |
| HSV Type-2 ($10^2$ copies/rxn) | 250 μL |

[a]Components for 100 assays per kit (50 uL per assay reaction volume) includes 40 type-specific control reactions
[b]10X = Core buffer (700 mM Tris, 400 mM KCl, 1% Tween) + 30 mM $MgCl_2$ (pH 8.5)
[c]5 mM each dNTP
[d]20 μM FAM-labeled IAC-specific MB + 10 μM TET-labeled HSV type-2 specific MB
[e]20 μM each primer + IAC plasmid (83.3 pg/mL, 75,000 copies/rxn)
[f]$10^5$ = 4000 copies/μL, $10^2$ = 4 copies/μL

TABLE 7[a]

| Material | Quantity |
|---|---|
| 10X PCR buffer[b] | 500 μL |
| 20 mM dNTPs[c] | 50 μL |
| 20 μM molecular beacons mix[d] | 175 μL |
| 40 μM primer mix[e] | 300 μL |
| 5 U/μL Taq2000 | 50 μL |
| HSV Type-specific controls[f]: | |
| HSV Type-1 ($10^5$ copies/rxn) | 250 μL |
| HSV Type-1 ($10^2$ copies/rxn) | 250 μL |
| HSV Type-2 ($10^5$ copies/rxn) | 250 μL |
| HSV Type-2 ($10^2$ copies/rxn) | 250 μL |

[a]Components for 100 assays per kit (50 uL per assay reaction volume) includes 40 type-specific control reactions
[b]10X = Core buffer (700 mM Tris, 400 mM KCl, 1% Tween) + 30 mM $MgCl_2$ (pH 8.5)
[c]5 mM each dNTP
[d]10 μM FAM-labeled HSV type-2-specific MB + 10 μM TET-labeled HSV type-1 specific MB
[e]20 μM each primer (83.3 pg/mL)
[f]$10^5$ = 4000 copies/μL, $10^2$ = 4 copies/μL The foregoing is merely illustrative of the invention and is not intended to limit the invention to the disclosed polynucleotides, methods and kits. Variation and changes are intended to be within the scope and nature of the invention which is defined by the appended claims.

---

What is claimed is:

1. A purified polynucleotide selected from the group consisting of SEQ ID NOS: 1–11.

2. A pair of polynucleotide primers for a polymerase chain reaction, wherein the primers comprise SEQ ID NO:1 and SEQ ID NO:2.

3. A method for HSV detection, comprising the steps of:
   (a) contacting a target nucleic acid with a polynucleotide comprising SEQ ID NO:4, wherein said target nucleic acid comprises a sequence complementary to said polynucleotide, wherein a hybrid forms between said target nucleic acid and said polynucleotide under conditions which permit formation of said hybrid; and
   (b) detecting said hybrid.

4. The method of claim 3 wherein said polynucleotide is labeled.

5. The method of claim 4 wherein said detecting step comprises detecting emission of fluorescence.

6. A method for HSV detection, comprising the steps of:
   (a) mixing a target nucleic acid with a polynucleotide for detecting HSV selected comprising SEQ ID NO:4, and a pair of polynucleotides for polymerase chain reaction comprising SEQ ID NO: 1 and SEQ ID NO:2, wherein said target nucleic acid comprises a sequence complementary to said polynucleotide for detecting HSV and a sequence complementary to said pair of polynucleotides for polymerase chain reaction;
   (b) incubating a mixture of step (a) under conditions which permit a polymerase chain reaction to generate a product comprising a sequence to said polynucleotide for detecting HSV and which permit formation of a hybrid between said polynucleotide for detecting HSV and said product; and
   (c) detecting said hybrid.

7. The method of claim 6 wherein said polynucleotide for detecting HSV is labeled.

8. The method of claim 7 wherein said detecting step comprises detecting emission of fluorescence.

9. A method for HSV detection, comprising the steps of:
   (a) contacting a target nucleic acid with a pair of polynucleotides selected from the group consisting of SEQ ID NO:3 and SEQ ID NO:4 or SEQ ID NO:3 and SEQ ID NO:3, wherein said target nucleic acid comprises a sequence complementary to at least one of said polynucleotide, wherein a hybrid forms between said target nucleic acid and at least one of said polynucleotide under conditions which permit formation of said hybrid; and
   (b) detecting said hybrid.

10. The method of claim 9 wherein said polynucleotides for detecting HSV are differentially labeled.

11. The method of claim 10 wherein said detecting step comprises detecting emission of fluorescence.

12. A method for HSV detection, comprising the steps of:
    (a) mixing a target nucleic acid with a pair of polynucleotides for detecting HSV selected from the group consisting of SEQ ID NO:3 and SEQ ID NO:4 or SEQ ID NO:3 and SEQ ID NO:3, and a pair of polynucleotides for polymerase chain reaction comprising SEQ ID NO: 1 and SEQ ID NO:2, wherein said target nucleic acid comprises a sequence complementary to at least one of said polynucleotides for detecting HSV and a sequence complementary to said pair of polynucleotides for polymerase chain reaction;
    (b) incubating a mixture of step (a) under conditions which permit a polymerase chain reaction to generate a product comprising a sequence of at least one of said polynucleotides for detecting HSV and which permit formation of a hybrid between at least one of said polynucleotide for detecting HSV and said product; and
    (c) detecting said hybrid.

13. The method of claim 12 wherein said polynucleotides for detecting HSV are differentially labeled.

14. The method of claim 13 wherein said detecting step comprises detecting emission of fluorescence.

* * * * *